United States Patent [19]

Burtscher et al.

[11] Patent Number: 5,679,571

[45] Date of Patent: Oct. 21, 1997

[54] RECOMBINANT D-HYDANTOINASE, A PROCESS FOR THE PRODUCTION AND USE

[75] Inventors: Helmut Burtscher, Habach; Gunter Lang, Tutzing; Friedrich Popp, Sindelsdorf, all of Germany

[73] Assignee: Boehringer Mannheim GmbH, Mannheim, Germany

[21] Appl. No.: 602,656

[22] Filed: Feb. 16, 1996

Related U.S. Application Data

[62] Division of Ser. No. 289,709, Aug. 12, 1994, Pat. No. 5,523,224.

[30] Foreign Application Priority Data

Aug. 27, 1993 [DE] Germany .................. 43 28 829.4

[51] Int. Cl.[6] .................. C12N 5/00; C12N 1/20; C12N 15/00; C07H 21/04
[52] U.S. Cl. .................. 435/325; 435/252.3; 435/252.33; 435/254.11; 435/254.21; 435/320.1; 536/23.2
[58] Field of Search .................. 435/252.3, 252.33, 435/254.11, 254.21, 325, 320.1; 536/23.2

[56] References Cited

U.S. PATENT DOCUMENTS

| 4,912,044 | 3/1990 | Jacob et al. | 435/172.3 |
|---|---|---|---|
| 5,523,224 | 6/1996 | Burtscher et al. | 435/231 |

OTHER PUBLICATIONS

Mukohara et al. (1994) A thermostable hydantoinase of Bacillus stearothermophilus NS 1122A: Cloning, sequencing, and high expression of the enzyme gene, and some properties of the expressed enzyme. Biosci. Biotechnol. Biochem. 58: 1621–1626.

*Primary Examiner*—Robert A. Was
*Assistant Examiner*—Lisa J. Hobbs
*Attorney, Agent, or Firm*—Felfe & Lynch

[57] ABSTRACT

A recombinant protein with D-hydantoinase activity which has the amino acid sequence SEQ ID NO 1 is obtainable in large amounts and has an improved temperature stability.

8 Claims, 1 Drawing Sheet

RECOMBINANT D-HYDANTOINASE, A PROCESS FOR THE PRODUCTION AND USE

This application is a Divisional of Ser. No. 08/289,709 filed Aug. 12, 1994, now U.S. Pat. No. 5,523,224.

The invention concerns a new recombinant D-hydantoinase, a process for its production and its use.

D-hydantoinases (dihydropyrimidinases, EC 3.5.2.2) are used to produce N-carbamoyl-D-amino acids. These compounds are important intermediate products for the production of D-amino acids (Morin et al., Appl. Microbiol. 35, 536–540 (1991), EP-B 0 219 034). D-amino acids are in turn important starting materials for the synthesis of the side chains of penicillins and semi-synthetic cephalosporins. The production of N-carbamoyl-D-amino acids is preferably carried out at higher temperatures since the hydantoins are then more soluble, the racemisation takes place more rapidly and the reaction is also accelerated. For this reason there is a need for thermostable D-hydantoinases.

A D-hydantoinase which is active at high temperatures (40°–90° C.) can be obtained from thermophilic microorganisms (DE-A 30 31 151). However, these thermophilic microorganisms are difficult to cultivate and grow poorly. In addition D-hydantoinase is only produced in very small amounts by these microorganisms.

A recombinant D-hydantoinase is described in EP-B 0 219 034. However, D-hydantoinase activity is only obtained in a small amount during expression of the DNA sequences described in EP-B 0 219 034.

BRIEF SUMMARY OF THE INVENTION

The object of the present invention was to provide a recombinant D-hydantoinase with a further improved temperature stability in large amounts.

This object is achieved by a protein which has D-hydantoinase activity and is characterized by the amino acid sequence SEQ ID NO 1.

DETAILED DESCRIPTION

Figure 1:
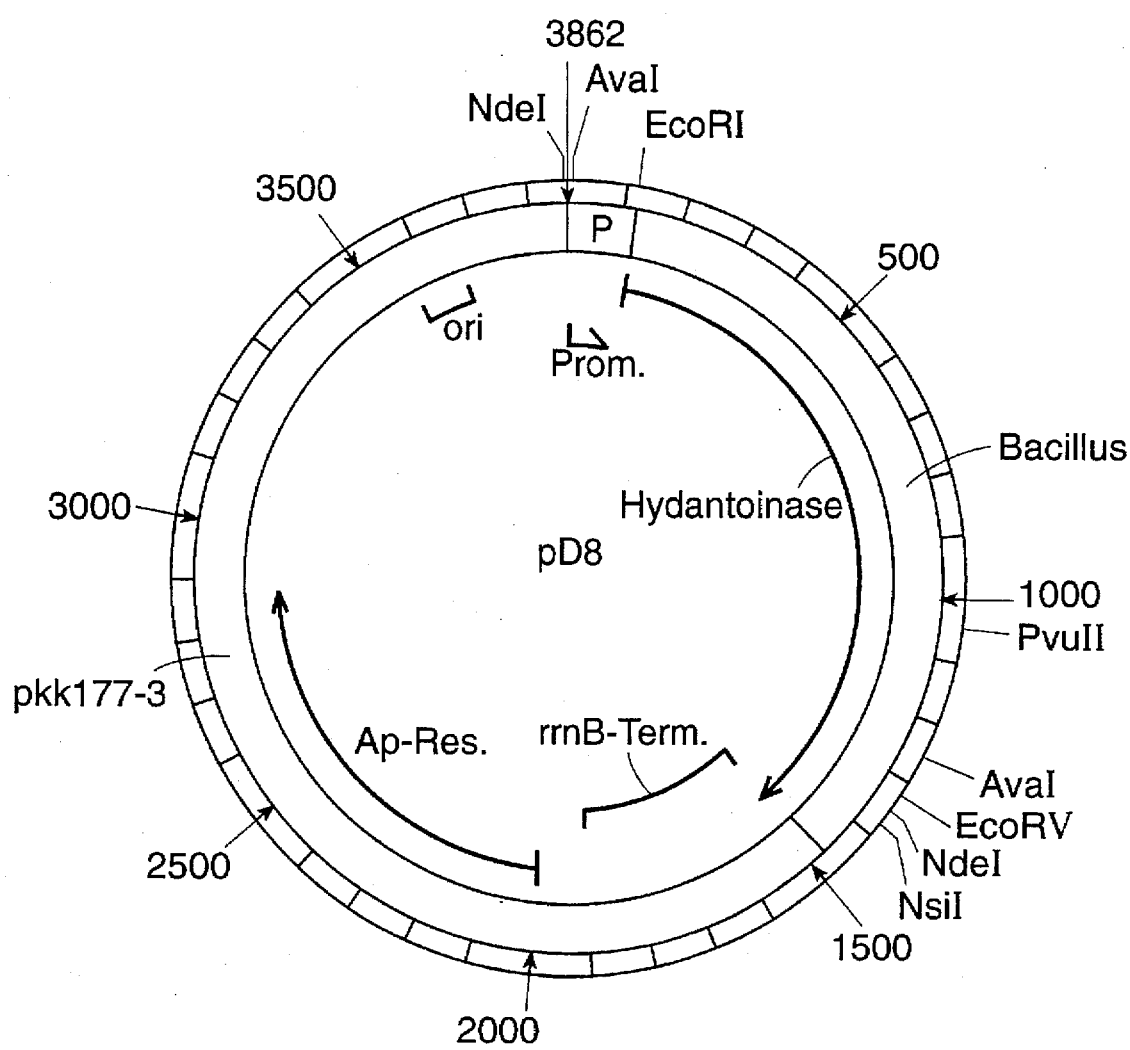
FIG. 1 presents a restriction endonuclease map of a plasmid used to express the D-hydantoinase of the invention.

The protein has
a) a pH optimum at ca. 8.2, an optimum for pH stability between ca. 6.5 and 9.0,
b) still has ca. 100% of the initial activity in 50 mmol/l Tris buffer, pH 7.8 at a concentration of 15 mg/ml after 20 minutes at 60° C. and still ca. 80% of the initial activity after 20 minutes at 65° C.,
c) is a polypeptide that does not occur naturally,
d) is the product of a prokaryotic expression of an exogenous DNA.

It surprisingly turned out that the enzyme according to the invention can be produced recombinantly in prokaryotes in large amounts, is readily soluble and has a high activity and good temperature stability.

The recombinant D-hydantoinase according to the invention differs from the native enzyme (wild-type enzyme) from for example thermophilic bacillus (DE-OS 30 31 151) and from the enzyme described in EP-B 0 219 034 with regard to the amino acid sequence at the C-terminus.

The enzyme according to the invention is 12 amino acids shorter than the wild-type enzyme and differs in the sequence of the last 6 amino acids. Compared to the enzyme described in EP-B 0 219 034, the enzyme according to the invention is 8 amino acids longer and differs in the sequence of the last 30 amino acids.

D-hydantoinases according to the invention are also understood as those proteins whose amino acid sequence differs slightly from SEQ ID NO 1. In this case amino acids can be substituted, deleted, derivatized or added.

A DNA is used for the recombinant production of D-hydantoinase according to the invention which codes for a protein with D-hydantoinase activity and is selected from the group
 a) the DNA sequence shown in sequence ID NO 2 or the complementary DNA sequence thereto,
 b) DNA sequences which due to the degeneracy of the genetic code, code for a protein which is also coded by one of the sequences defined in a).

A DNA sequence of sequence ID NO 2 is preferably used.

The DNA sequences can be slightly modified in a manner familiar to a person skilled in the art. For example degenerate codons can be replaced by other codons which code for the same amino acid. Furthermore additional codons can be inserted at the 5' and the 3' end or also within the sequences or individual codons or groups of codons can be deleted provided that the DNA variants obtained in this manner only differ slightly from the sequences according to the invention, hybridize with these sequences under the usual conditions (Sambrook et al., Molecular cloning, A Laboratory Manual, Cold Spring Harbor Laboratory Press, New York 1989) and the coded protein has D-hydantoinase activity.

The invention in addition concerns a process for the production of a recombinant D-hydantoinase by transformation of a suitable prokaryotic host cell (e.g. E. coli, Saccharomyces cerevisiae) with a DNA according to the invention which is present in a suitable expression system, culture of the transformed host cells and isolation of the D-hydantoinase formed from the cells or the cell supernatant.

The transformation of the host cells used for the recombinant production is carried out according to known methods (Sambrook et al. 1989). The transformed host cells are cultured under conditions which allow an expression of the D-hydantoinase gene. Depending on the expression vector used, it may be necessary to add an inductor (e.g. lactose or isopropyl-β-D-thio-galactopyranoside (IPTG)) in a known manner to the culture medium. The isolation of the recombinant D-hydantoinase from the cell supernatant or the cells is carried out in a known manner.

Using this process it is possible to obtain recombinant, active D-hydantoinase in a yield of up to $10^6$ U/1.5 kg biomass.

Lysis and purification of the recombinantly produced D-hydantoinase can be carried out according to methods familiar to a person skilled in the art. The biomass obtained after fermentation is preferably disrupted in a high pressure homogenizer, the crude extract fractionated with ammonium sulfate and incubation at ca. 60° C. (heat step).

The invention in addition concerns a process for cleaving a racemic hydantoin into the corresponding N-carbamoyl-D-amino acid which is characterized in that the racemic hydantoin is incubated with a D-hydantoinase according to the invention at a temperature of 50°–80° C. and the N-carbamoyl-D-amino acid that is formed is subsequently isolated and if desired purified from the reaction mixture according to methods familiar to a person skilled in the art.

All genetic engineering methods such as e.g. expression, DNA modification, cloning and isolation of the recombinant protein can be carried out according to methods familiar to a person skilled in the art such as those described in Ausubel, F. M., et al., Current Protocols in Molecular Biology, Wiley, New York 1992; Sambrook et al. (1989) or Davis, L. G., Methods in Molecular Biology, Elsevier, Amsterdam, NL, 1986.

The invention is elucidated in more detail by the following examples, the sequence protocol and the figure:

EXAMPLE 1

Plasmid construction

A D-hydantoinase gene is isolated from *Bacillus thermoglucosidasius* (wild type) using two primers (Hyd1 and Hyd2) and inserted after restriction with the restriction enzymes EcoRI and HindIII into a suitable expression vector for expression in *E. coli* (pKK177-3, DSM 3062).

Hyd1: GGAATTCTATGACAAAAATAAT-
AAAAAATGG                                    (SEQ ID NO 3)

Hyd2: GCGGATCCAAGCTTTTAAATATT-
GGCCGTACCC                                   (SEQ ID NO 4)

If a base is deleted from the HindIII cleavage site (AAGCTT→AAGCT) then a reading frame is formed that can be translated into a protein having SEQ ID NO 1 (FIG. 1).

The resulting plasmid pD8 contains SEQ ID NO 2 as the protein-coding sequence under the control of an IPTG-inducible promoter. In this plasmid the promoter can be replaced by other promoters such as e.g. by the lac promoter, mgl promoter (EP-A 0 316 370) or by the promoters described in EP-A.0 186 069 and EP-A 0 303 925.

EXAMPLE 2

Description of the fermentation process for recombinant hydantoinase from *E. coli*

*E. coli* HB 101 (DSM 1607) is used as the host organism which contains pD8 as well as the lacI gene on a compatible plasmid.

The precultures were cultured in LB medium with double selection pressure (kanamycin and ampicillin) starting from paillettes stored in liquid nitrogen.

The inoculation volume for the main culture is 1–10% by volume. The main components of the HK medium are yeast extract and glucose. The medium is adjusted with $K_2HPO_4$ to pH 7.6–7.8 before the inoculation.

Further essential components of the medium are Mn and Mg salts. They are necessary for the activity and stability of the hydantoinase. The salts are sterilized separately and added separately to the medium. Only a small amount (ca. 20%) is added first, the main amount is added via a glucose dosage which is used as a regulator of acidity.

In order to avoid formation of inclusion bodies (IBs), induction with a small amount of IPTG (<1 mmol) is not carried out until an $OD_{578}$ of 10. The fermentation temperature is 32° C. In addition above $OD_{578}$=30 a limiting dose of yeast extract is added to limit the growth rate.

By regulating and limiting the specific growth rate via the dosage rate, it is possible to almost completely suppress IB formation and achieve a high yield of biomass. The pH value is regulated at 7.0–7.2. In order to suppress undesired acid formation the dissolved oxygen value $pO_2$ is kept at >10% by means of the stirrer speed, inlet air control, dosage rate and/or pressure.

An $OD_{578}$ of 120–140 is achieved after a fermentation period of ca. 40 hours. This represents a biomass yield of 45–50 g dry weight/l. The hydantoinase activity is in this case >1 MU/l which corresponds to an expression rate of >10 g/l of active, soluble hydantoinase at a specific activity of ca. 100 U/mg.

EXAMPLE 3

3.1 Disruption 1.5 kg wet biomass is suspended in 6 liters cold 50 mmol/l TRIS/HCl buffer pH 8.5 and disrupted with a high pressure homogenizer from the APV Gaulin GmbH Company at 1200 bar. The suspension is subsequently cooled to +4° C. and centrifuged at high speed at ca. 25,000 x g in a Sorvall centrifuge.

3.2 Ammonium sulfate fractionation

Solid ammonium sulfate is added to the crude extract up to a concentration of 1.3 mol/l, the precipitate is discarded by centrifugation at high speed. The supernatant is precipitated further with ammonium sulfate up to a concentration of 2.5 mol/l and the precipitate is again centrifuged at high speed.

3.3 Heat step

The precipitate of the ammonium sulfate precipitation is dissolved with 50 mmol/l TRIS/HCl buffer pH 8.5 and adjusted to a protein concentration of 10 mg/ml. The enzyme solution is heated to 56° C. and kept at this temperature for 30 minutes; subsequently it is cooled to +4° C. and the precipitate is centrifuged.

The yield is ca. $1 \times 10^6$ units with a specific activity of 35 U/mg protein.

3.4 Comparison with the state of the art

Table 1 shows a comparison of the activities expressed per liter for the known hydantoinases and for the enzyme according to the invention.

TABLE 1

| D-hydantoinase | Activity in kU/l |
| --- | --- |
| according to DE-A 30 31 151 (wild type) | 0.10 |
| according to EP-B 0 219 034 | 0.56 |
| according to the invention | 1000 |

We claim:

1. Isolated nucleic acid molecule which codes for a protein consisting of the amino acid sequence set forth in SEQ ID NO: 1, wherein said protein has D-hydantoinase activity, and retains about 100% of said D-hydantoinase activity after 20 minutes at 60° C., when present in a 50 mmol/l Tris buffer, pH 7.8, at a concentration of 15 mg/ml, and retains about 80% of said D-hydantoinase activity after 20 minutes at 65° C., in a 50 mmol/l Tris buffer at pH 7.8.

2. The isolated nucleic acid molecule of claim 1, selected from the group consisting of:

(i) an isolated nucleic acid molecule having the nucleotide sequence of SEQ ID NO: 2, and
  (ii) an isolated nucleic acid molecule complementary to SEQ ID NO: 2.

3. Recombinant vector comprising the isolated nucleic acid molecule of claim 1, operably linked to a promoter.

4. Isolated host cell transformed or transfected with the isolated nucleic acid molecule of claim 1.

5. The isolated host cell of claim 4, wherein said cell is prokaryotic.

6. The isolated host cell of claim 4, wherein said cell is eukaryotic.

7. The isolated host cell of claim 5, wherein said cell is *E. coli*.

8. The isolated host cell of claim 6, wherein said cell is Saccharomyces.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 460 amino acids
        ( B ) TYPE: amino acid ( C ) STRANDEDNESS: single
( D ) TOPOLOGY: linear ( x i ) SEQUENCE DESCRIPTION: SEQ ID NO: 1:

```
Met  Thr  Lys  Ile  Ile  Lys  Asn  Gly  Thr  Ile  Val  Thr  Ala  Thr  Asp  Thr
 1                  5                      10                      15

Tyr  Glu  Ala  Asp  Leu  Leu  Ile  Lys  Asp  Gly  Lys  Ile  Ala  Met  Ile  Gly
               20                      25                      30

Gln  His  Leu  Glu  Glu  Lys  Gly  Ala  Glu  Val  Ile  Asp  Ala  Lys  Gly  Cys
          35                      40                      45

Tyr  Val  Phe  Pro  Gly  Gly  Ile  Asp  Ser  His  Thr  His  Leu  Asp  Met  Pro
     50                      55                      60

Phe  Gly  Gly  Thr  Val  Thr  Lys  Asp  Asp  Phe  Glu  Ser  Gly  Thr  Ile  Ala
 65                      70                      75                      80

Ala  Ala  Phe  Gly  Gly  Thr  Thr  Ile  Ile  Asp  Phe  Cys  Leu  Thr  Asn
                    85                      90                      95

Lys  Gly  Glu  Pro  Leu  Lys  Lys  Ala  Ile  Glu  Thr  Trp  His  Asn  Lys  Ala
               100                     105                     110

Lys  Gly  Lys  Ala  Val  Ile  Asp  Tyr  Gly  Phe  His  Leu  Met  Ile  Ser  Glu
          115                     120                     125

Ile  Thr  Asp  Asp  Val  Leu  Glu  Glu  Leu  Pro  Lys  Val  Ile  Ala  Glu  Glu
     130                     135                     140

Gly  Ile  Thr  Ser  Phe  Lys  Val  Phe  Met  Ala  Tyr  Lys  Asn  Val  Phe  Gln
145                     150                     155                     160

Ala  Asp  Asp  Gly  Thr  Leu  Tyr  Arg  Thr  Leu  Val  Ala  Ala  Lys  Glu  Leu
               165                     170                     175

Gly  Ala  Leu  Val  Met  Val  His  Ala  Glu  Asn  Gly  Asp  Val  Ile  Asp  Tyr
          180                     185                     190

Leu  Thr  Lys  Lys  Ala  Leu  Ala  Glu  Gly  Asn  Thr  Glu  Pro  Ile  Tyr  His
     195                     200                     205

Ala  Leu  Thr  Arg  Pro  Pro  Glu  Val  Glu  Gly  Glu  Ala  Thr  Gly  Arg  Ala
     210                     215                     220

Cys  Gln  Leu  Thr  Glu  Leu  Ala  Gly  Ser  Gln  Leu  Tyr  Val  Val  His  Val
225                     230                     235                     240

Thr  Cys  Ala  Gln  Ala  Val  Glu  Lys  Ile  Ala  Gln  Ala  Arg  Asn  Lys  Gly
               245                     250                     255

Leu  Asp  Val  Trp  Gly  Glu  Thr  Cys  Pro  Gln  Tyr  Leu  Val  Leu  Asp  Gln
               260                     265                     270

Ser  Tyr  Leu  Glu  Lys  Pro  Asp  Phe  Glu  Gly  Ala  Lys  Tyr  Val  Trp  Ser
          275                     280                     285

Pro  Pro  Leu  Arg  Glu  Lys  Trp  His  Gln  Glu  Val  Leu  Trp  Asn  Ala  Leu
     290                     295                     300

Lys  Asn  Gly  Gln  Leu  Gln  Thr  Leu  Gly  Ser  Asp  Gln  Cys  Ser  Phe  Asp
305                     310                     315                     320

Phe  Lys  Gly  Gln  Lys  Glu  Leu  Gly  Arg  Gly  Asp  Phe  Thr  Lys  Ile  Pro
               325                     330                     335

Asn  Gly  Gly  Pro  Met  Val  Glu  Asp  Arg  Val  Ser  Ile  Leu  Phe  Ser  Glu
               340                     345                     350

Gly  Val  Lys  Lys  Gly  Arg  Ile  Thr  Leu  Asn  Gln  Phe  Val  Asp  Ile  Met
          355                     360                     365

Ser  Thr  Arg  Ile  Ala  Lys  Leu  Phe  Gly  Leu  Phe  Pro  Arg  Lys  Gly  Thr
     370                     375                     380

Ile  Ala  Val  Gly  Ser  Asp  Ala  Asp  Leu  Val  Ile  Phe  Asp  Pro  Asp  Ile
385                     390                     395                     400
```

| Glu | Arg | Val | Ile | Ser 405 | Ala | Glu | Thr | His 410 | His | Met | Ala | Val | Asp 415 | Tyr | Asn |
| Ala | Phe | Glu | Gly 420 | Met | Lys | Val | Thr | Gly 425 | Glu | Pro | Val | Ser | Val 430 | Leu | Cys |
| Arg | Gly | Glu 435 | Phe | Val | Val | Arg | Asp 440 | Lys | Gln | Phe | Val | Gly 445 | Lys | Pro | Gly |
| Tyr | Gly 450 | Gln | Tyr | Leu | Lys | Ala 455 | Gly | Cys | Phe | Gly | Gly 460 | | | | |

(2) INFORMATION FOR SEQ ID NO: 2:

(i) SEQUENCE CHARACTERISTICS:
        (A) LENGTH: 1383 base pairs
        (B) TYPE: nucleic acid
        (C) STRANDEDNESS: single
        (D) TOPOLOGY: linear (xi) SEQUENCE DESCRIPTION: SEQ ID NO: 2:

```
ATGACAAAAA TAATAAAAAA TGGAACGATT GTTACCGCAA CCGATACGTA TGAAGCGGAC      60
TTGCTCATTA AGACGGAAA  AATTGCCATG ATAGGCCAAC ATTTAGAAGA AAAAGGCGCT     120
GAAGTGATTG ATGCCAAGG  CTGTTACGTA TTTCCAGGCG GTATTGATTC GCACACGCAT     180
TTAGATATGC CGTTTGGCGG CACGGTGACA AAGGATGATT TCGAATCTGG AACGATTGCG     240
GCGGCATTTG CGGAACAAC  GACCATCATC GACTTTTGTT TAACGAATAA AGGGGAGCCA     300
TTAAAAAAAG CGATTGAAAC TTGGCACAAC AAAGCGAAGG GAAAAGCGGT TATTGATTAT     360
GGCTTCCATT TAATGATTAG CGAAATTACG GATGACGTAT TAGAAGAGCT GCCAAAAGTC     420
ATTGCCGAAG AAGGGATAAC ATCCTTTAAA GTGTTTATGG CGTATAAAAA CGTATTTCAG     480
GCAGATGATG GAACGTTATA CCGCACGCTA GTGGCTGCCA AAGAACTTGG CGCGCTTGTC     540
ATGGTTCATG CGGAAAATGG GGATGTGATT GATTACTTAA CGAAAAAAGC GCTTGCGGAA     600
GGGAATACGG AGCCGATTTA CCATGCTTTA ACGCGGCCTC CAGAAGTAGA AGGAGAAGCG     660
ACCGGGCGCG CCTGTCAATT GACAGAGCTT GCCGGTTCAC AACTTTACGT TGTTCACGTG     720
ACATGTGCGC AAGCGGTGGA AAAAATTGCA CAAGCGCGCA ATAAAGGGTT GGATGTGTGG     780
GGAGAAACGT GTCCGCAATA TCTTGTTCTC GACCAATCGT ATTTAGAAAA GCCTGATTTT     840
GAAGGCGCGA AATATGTTTG GTCCCCTCCG CTTCGTGAAA AATGGCATCA AGAAGTATTG     900
TGGAATGCGC TGAAAAACGG CCAGCTGCAA ACGCTTGGAT CGGACCAATG TTCATTTGAC     960
TTTAAAGGCC AAAAAGAACT TGGCAGAGGA GATTTTACTA AAATTCCAAA CGGCGGGCCG    1020
ATGGTCGAGG ATCGGGTCAG CATTCTTTTC AGTGAAGGGG TTAAAAAAGG AAGAATCACG    1080
TTAAATCAAT TTGTCGATAT TATGTCGACA AGAATTGCCA AATTGTTCGG GTTATTCCCG    1140
AGAAAAGGAA CGATCGCGGT AGGTTCAGAC GCAGACTTAG TCATTTTTGA CCCGGATATC    1200
GAACGGGTGA TTTCGGCGGA AACACACCAT ATGGCCGTCG ACTATAATGC ATTTGAAGGA    1260
ATGAAAGTAA CGGGTGAACC GGTATCGGTT CTGTGCAGAG GCGAATTTGT TGTCCGTGAT    1320
AAACAATTTG TCGGAAAACC AGGGTACGGC CAATATTTAA AAGCTGGCTG TTTTGGCGGA    1380
TGA                                                                 1383
```

(2) INFORMATION FOR SEQ ID NO: 3:

(i) SEQUENCE CHARACTERISTICS:
        (A) LENGTH: 31 base pairs
        (B) TYPE: nucleic acid
        (C) STRANDEDNESS: single
        (D) TOPOLOGY: linear ( x i ) SEQUENCE DESCRIPTION: SEQ ID NO: 3:

GGAATTCTAT GACAAAAATA ATAAAAAATG G    31

( 2 ) INFORMATION FOR SEQ ID NO: 4:

( i ) SEQUENCE CHARACTERISTICS:
     ( A ) LENGTH: 33 base pairs
     ( B ) TYPE: nucleic acid
     ( C ) STRANDEDNESS: single
     ( D ) TOPOLOGY: linear ( x i ) SEQUENCE DESCRIPTION: SEQ ID NO: 4:

GCGGATCCAA GCTTTTAAAT ATTGGCCGTA CCC    33